(12) United States Patent
Abraham et al.

(10) Patent No.: US 6,534,501 B2
(45) Date of Patent: Mar. 18, 2003

(54) ALLOSTERIC INHIBITORS OF PYRUVATE KINASE

(75) Inventors: Donald J. Abraham, Midlothian, VA (US); Changging Wang, Richmond, VA (US); Richmond Danso-Danquah, Richmond, VA (US); James C. Burnett, Ashland, VA (US); Gajanan S. Joshi, Glen Allen, VA (US); Stephen J. Hoffman, Carlisle, MA (US)

(73) Assignees: Allos Therapeutics, Inc., Denver, CO (US); Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/799,873

(22) Filed: Mar. 7, 2001

(65) Prior Publication Data

US 2001/0046997 A1 Nov. 29, 2001

Related U.S. Application Data

(63) Continuation-in-part of application No. 09/046,643, filed on Mar. 24, 1998, now Pat. No. 6,214,879.

(51) Int. Cl.[7] ............... A61K 31/505; A61K 31/54; A61K 31/535; A61K 31/38; A61K 31/19
(52) U.S. Cl. ............... 514/228; 514/259; 514/411; 514/239.5; 514/237.5; 514/445; 514/438; 514/447; 514/230.5; 514/262; 514/266; 514/250; 514/542; 514/575; 514/595; 514/579

(58) Field of Search ................ 514/259, 411, 514/239.5, 237.5, 445, 438, 447, 228.8, 230.5, 262, 266, 250, 542, 575, 595

(56) References Cited

U.S. PATENT DOCUMENTS

| | | | | | |
|---|---|---|---|---|---|
| 488,995 | A | * | 1/1893 | Abraham et al. | 165/87 |
| 4,704,402 | A | * | 11/1987 | Abraham et al. | 514/543 |
| 4,751,244 | A | * | 6/1988 | Abraham et al. | 514/563 |
| 5,122,539 | A | * | 6/1992 | Abraham et al. | 514/486 |
| 5,382,680 | A | * | 1/1995 | Abraham et al. | 560/42 |
| 5,599,974 | A | * | 2/1997 | Abraham et al. | 560/130 |

* cited by examiner

*Primary Examiner*—Theodore J. Criares
(74) *Attorney, Agent, or Firm*—Whitham, Curtis & Christofferson, P.C.

(57) ABSTRACT

Chemical structures have been identified which allosterically modify pyrvate kinase and inhibit enzymatic activity. These compounds can be used as pharmaceuticals in the treatment of a wide variety of diseases and disorders where influencing metabolic processes is beneficial, such as the glycolytic pathway, all pathways which use ATP as an energy source, and all pathways which involve 2,3-diphosphoglycerate related to the delivery of oxygen by modifying hemoglobin's oxygen affinity, treatments of tumor and cancer and Alzheimer's disease (AD).

12 Claims, 7 Drawing Sheets

|  |  |  | Compound # | | | | | | | | | | | |
|---|---|---|---|---|---|---|---|---|---|---|---|---|---|---|
| Conc. (μM) | Control DMSO | ATP | 1 | 2 | 3 | 4 | 5 | 6 | 7 | 8 | 9 | 10 | 11 | 12 |
|  |  |  | % PK Activity | | | | | | | | | | | |
| 50 | 100% | 26.6% | 56 | 59 | 75 | 62 | 10 | 26 | 25 | 22 | 15 | 10 | 11 | 19 |
| 25 | 100% | 46.3% | 66 | 36 | 86 | 44 | 17 | 44 | 29 | 37 | 29 | 19 | 27 | 31 |
| 12.5 | 100% | 68.2% | 75 | 20 | 100 | 26 | 41 | 69 | 44 | 63 | 56 | 38 | 49 | 57 |
| 6.25 | 100% | 78.8% | 96 | 12 | 100 | 19 | 63 | 74 | 61 | 79 | 87 | 60 | 66 | 91 |
| 3.125 | 100% | 85.7% | 100 | 6 | 100 | 13 | 71 | 93 | 80 | 92 | 97 | 79 | 87 | 100 |

ALLOSTERIC INHIBITORS OF PYRUVATE KINASE

RELATED APPLICATION

This is a continuation-in-part of Ser. No. 09/046,643 filed Mar. 24, 1998 now U.S. Pat. No. 6,214,879 B1.

BACKGROUND OF THE INVENTION

1. Field of the Invention

The invention is generally related to pharmaceuticals, which are useful for allosterically modifying pyruvate kinase.

2. Description of the Prior Art

Mammalian pyruvate kinase (PK) is a key regulatory glycolytic enzyme that exhibits allosteric kinetic behavior. The basic mechanism of the allosteric regulation of PK at the molecular level is still not known. There are reports that PK undergoes conformational changes and that the changes involve domain events. PK is found in all cells and tissues. It catalyzes the conversion of phospho-enolpyruvate (PEP) and adenosine diphosphate (ADP) into pyruvate and adenosine triphosphate (ATP), as shown in reaction scheme 1.

$$\text{PEP} + \text{Mg.ADP} + \text{H}^+ \rightarrow (\text{Mg}^{2+}, \text{K}^+) \rightarrow \text{Mg.ATP} + \text{Pyruvate} \quad (1)$$

The reaction proceeds in two steps. First, the 2-phosphate is removed from PEP to yield ATP and the enolate ion form of pyruvate. The second step involves the protonation and tautomerization of the ion to yield the keto form of pyruvate. The enzyme requires three cation cofactors, two divalent ($Mg^{2+}$ or $Mn^{2+}$) and one monovalent ($K^+$). Positive factors of PK include fructose 1,6 diphosphate, PEP, and low pH. Negative factors of PK include ATP, high pH, and glycogenic amino acids such as alanine and phenylalanine. The products of reaction scheme 1, pyruvate and ATP, are involved in a wide variety of metabolic pathways; therefore, PK can be considered a key enzyme in the glycolytic pathway as well as many other pathways in the cellular metabolism.

In mammals, PK has four isoenzymes, which are identified as M-1, M-2, L and R type. The R type PK exists exclusively in red blood cells and its biochemical properties change with cell maturation. Congenital R-PK deficiency in erythrocytes is one of the most frequent enzymopathies involving the glycolytic pathway. It is an autosomal recessive disorder, and in hemozygotes, causes nonspherocytic hemolytic anemia. Heterozygotes do not show symptoms of hemolytic anemia, but have lowered residual PK activity, with increased 2,3-diphosphoglycerate (2,3-DPG) and fairly stable ATP levels. Thus, it appears quite possible that similar results will be obtained pharmacologically from partial inhibition of erythrocyte PK. Because ATP can be synthesized in erythrocytes only by glycolysis, a decreased PK activity causes severe disturbances of the erythrocyte energy metabolism and leads to greatly diminished lifetime of the red blood cells.

SUMMARY OF THE INVENTION

It is an object of this invention to provide pharmaceuticals suitable for allosterically modifying PK.

It is another object of this invention to use a family of pharmaceuticals to regulate the 2,3-DPG and ATP levels in vivo.

It is yet another object of this invention to use a family of pharmaceuticals to regulate the glycolytic pathway in vivo.

According to the invention, a family of compounds has been identified which allosterically modify pyruvate kinase. A compound within the family will be useful for the delivery of additional oxygen to tissues by increasing the 2,3-DPG concentration in vivo, and this can be useful in a wide variety of clinical conditions and disease states including radiation oncology, whole body and tissue hypothermia, hypoxia, chronic hypoxia, sepsis, wound healing, diabetic ulcers, pressure sores, tissue transplants, stroke, shock, cardiovascular ischemia and angina applications, acute respiratory distress syndrome (ARDS), chronic respiratory insufficiency, pulmonary fibrosis, interstitial lung disease, peripheral vascular disease (e.g., intermittent claudication), ischemia, including Alzheimer's disease (AD). PK contributes to the establishment of steady-state levels of 2,3-DPG, which is important since 2,3-DPG is an allosteric effector of oxygen binding to hemoglobin. PK was found to have an inverse relationship with 2,3-DPG levels in human erythrocytes. An increase in the level of 2,3-DPG induces a rightward shift of the oxygen-hemoglobin dissociation curve, indicating that the quaternary conformational equilibrium of hemoglobin is perturbed toward the T, or deoxygenated state. In other words, oxygen is more quickly being delivered from blood to tissues. Similarly, a decrease in the level of 2,3-DPG concentration induces a leftward shift of the oxygen-hemoglobin dissociation curve and shifts the allosteric equilibrium to the R, or oxygenated state. Such agents will be useful as antisickling agents. Increasing erythrocyte 2,3-DPG concentrations through the intervention of PK inhibition will find use in many clinical settings where more delivery of tissue oxygenation is desired.

A chemical modification of hemoglobin in vivo may provide an exciting alternative in the treatment of stroke in humans by enhancing oxygen delivery and reducing penumbral injury. Our past studies with allosteric inhibitors have produced exciting clinical results in treating acute hypoxia. However, chronic treatment of hypoxia with hemoglobin allosteric effectors is limited due to the high daily doses required to treat the large amount of Hb in red cells (5 mM in red cells). An alternate method to treat chronic hypoxia would be to inhibit the breakdown of the natural allosteric effector of Hb, 2,3-DPG. The much lower preponderance of red cell pyruvate kinase to Hb levels makes this an interesting target for treating chronic hypoxia. Besides the obvious chronic hypoxic diseases, treatment of AD is practically unknown as a focus for hypoxic therapy. However, Regelson and Harkins have pinpointed studies that firmly indicate that an increase in oxygen to the brain of AD patients may well improve the degree of severity of the disease. Regelson, W., Harkins, S. W., "Amyloid is not a tombstone"—a summation. The primary role for cerebrovascular and CSF dynamics as factors in Alzheimer's disease (AD): DMSO, fluorocarbon oxygen carriers, thyroid hormonal, and other suggested therapeutic measures, *Ann. NY Acad. Sci.* 826: 348–374 (1997). Pappas et al. have shown that chronic low-grade ischemia in rats can damage learning and memory—resembling clinical AD. Pappas, B. A., Davidson, C. M., Bennett, S. A., de la Torre, J. C., Fortin, T., Tenniswood, M. P., Chronic ischemia: memory impairment and neural pathology in the rat, *Ann. NY Acad. Sci.* 826:498–501 (1997). Olichney et al. have found clinical correlations between cerebral hemorrhage, infarction, and later amyloid vascular deposits, suggesting that amyloid in the vessel wall can contribute to ischemic pathology. Olichney, J. M., Ellis, R. J., Katzman, R., Sabbagh, M. N., Hansen, L., Types of cerbrovascular lesions associated with severe cerebral amyloid angiopathy in Alzheimer's disease, Ann. NY Acad. Sci. 826: 493–497 (1997). Cohen et al. support this work in showing that AD vascular pathology relates to angiopathy with amyloid adventitiously extending from the small vessels as an intrinsic part of the blood vessel wall. Cohen, D. L., Hedera, P., Premkumar, D. R., Friedland, R. P., Kalaria, R. N., Amyloid-beta protein angiopathies masquerading as Alzheimer's disease? Ann. NY Acad. Sci. 826:390–395 (1997). Other work also suggests that defects in cerebral vascular blood flow are directly and indirectly associated with AD. Moroney, J. T., Bagiella, E., Hachinski, V. C., Molsa, P. K., Gustafson, L., Brun, A., Fischer, P., Erkinjuntti, T., Rosen, W., Paik, M. C., Tatemichi, T. K., Desmond, D. W., Misclassification of dementia subtype using the Hachinski ischemic score: results of a meta-analysis of patients with pathologically verified dementias, Ann. NYAcad. Sci. 826:490–492 (1997); Hoyer, S., Models of Alzheimer's disease: cellular and molecular aspects, J. Neural Transm. Suppl. 49:11–21 (1997). Decreased blood flow (and thus decreased oxygen delivery) is directly related to the severity of AD. To date, it has not been clinically possible to increase oxygen delivery to brain, except for the acute use of an allosteric effector of hemoglobin. Teicher, B. A., Wong, J. S., Takeuchi, H., Gravelin, L. M., Ara, G., Buxton, D., Allosteric effectors of hemoglobin as modulators of chemotherapy and radiation therapy in vitro and in vivo, Cancer Chemother. Pharmocol, 42:24–30 (1998). Therefore, these compounds could also be of use in partial or even a higher degree of success in treatment of brain disorders such as AD and stroke. Also, the blood brain barrier would not restrict the efficacy of allosteric PK inhibitors as the effectors do not have to cross the blood brain barrier, but will act directly on PK in the red cell to increase oxygen delivery.

BRIEF DESCRIPTION OF THE DRAWINGS

The foregoing and other objects, aspects and advantages will be better understood from the following detailed description of the preferred embodiments of the invention with reference to the drawings, in which:

FIG. 3 shows chemical structures of various allosteric inhibitors. Structures in FIGS. 3a–3f are allosteric inhibitors with the phenylalanine of FIG. 3f being the control.

DETAILED DESCRIPTION OF THE PREFERRED EMBODIMENTS OF THE INVENTION

A family of compounds has been identified which allosterically inhibit pyruvate kinase. FIGS. 3a–f show the chemical structures of the compounds tested within the family and Example 3 describes the synthesis of these compounds. Example 1 explains how the PK was isolated and purified, and Example 2 discusses the test procedures used. Table 1 shows the effect of various allosteric inhibitors on PK activity.

TABLE 1

| Compound Name | Concentration (mM) | % PK Inhibition |
| --- | --- | --- |
| L-Phenylalanine | 10 | 15 |
| L-Phenylalanine | 30 | 72 |
| TB 32 | 0.5 | 48 |
| TB 32 | 2 | 77 |
| TB 32 | 3 | 80 |
| TB 88 | 0.5 | 16 |
| TB 88 | 2.5 | 28 |
| TB 154 | 0.5 | 19 |
| TB 154 | 2 | 28 |
| TDD 57 | 0.5 | 36 |
| CA-GSJ-2 | 0.5 | 36 |

As can be seen from Table 1, TB 32 can have the same or greater inhibitory effect on PK as phenylalanine at an order of magnitude less concentration. Hence TB 32 is one of the most potent inhibitors of PK discovered to date. Furthermore, the remaining data in Table 1 show that the other compounds within the family contemplated by this invention are significantly more potent inhibitors of PK then phenylalanine.

Derivatives of the compounds can be made which will also exhibit the same or enhanced allosteric effects on PK. These derivatives might advantageously be formed at the carboxylic acid moiety (by replacement of the hydrogen), but may also be configured at the aldehyde or be ionic in nature. These derivatives can include the substitution of salt or metal cations for hydrogen groups, such as sodium, potassium, lithium, ammonium, and alkali and alkaline metals (Mn and Mg, etc), or the formation of ester or ether derivatives at the hydrogen groups such as $C_{1-12}$ alkyl groups, or involve similar substitutions.

This invention contemplates the use of the allosteric modifiers of PK to treat a wide variety of disorders by influencing metabolic pathways such as the glycolytic pathway, pathways that use ATP as an energy source, and pathways affected by 2,3-DPG. For exemplary purposes only, the compounds may be used in the following clinical settings: radiation oncology, transplantation, hypothermia (whole body and tissue), resuscitation from hemorrhagic shock, wound healing, tissue transplantation, treatment of diabetic ulcers and chronic leg ulcers, stroke, during bypass surgery, ischemia, cardiovascular/angina applications, Alzheimer's disease, ARDS, chronic respiratory insufficiency, pulmonary fibrosis, interstitial lung disease, chronic obstructive pulmonary disease, peripheral vascular disease (e.g., intermittent claudication), sepsis, anticancer therapy, sickle cell anemia, etc. The compounds might also be used to counteract aging of stored blood by impacting the rate of release of 2,3-DPG from the blood. The allosteric modifier compounds can be added directly to whole blood or packed cells extra corporally or be provided to the patient directly by i.p., i.v., i.m., oral, inhalation (aerosolized delivery), transdermal, sublingual and other delivery routes. Appropriate pharmaceutical preparations can include liquid and solid materials in the preparation of injectable or orally administered (tablets and capsules) or other delivery routes. Examples of solid diluents and excipients include lactose starch, disintegrating agents, and coatings. Buffers (preferably which render the composition isotonic), carrier fluids (including water, oils, etc.), surfactants (Tween, oleic acid, sorbitan trioleate, etc.), preservatives (parabens, benzalkonium chloride, EDTA, etc.), and the like may all be combined with one or more (combinations of compounds being specifically contemplated herein) PK allosteric modifiers to produce a pharmaceutically acceptable (stable, safe and efficacious) product which can be delivered to a patient or blood sample to allosterically modify PK. Depending upon the disorder to be treated, an inhibitor or an activator of PK will be chosen for administration. The dose will be a function of the patient (sex, age, etc.), the condition being treated, the route of delivery, and other factors. The dose should be sufficient to either activate or inhibit pyruvate kinase activity (depending on the allosteric modifier chosen (e.g., inhibitor or activator).

EXAMPLE 1

Method of Purification of PK

Human R-PK is usually prepared from whole blood according to the method described in by Kohn et al., *Meth. Enzymol.* 90:131–140. This method uses ammonium sulfate precipitation followed by affinity chromatography with Blue Dextran-Sepharose. A major drawback of this method is the low binding capacity of the resin used with PK under the conditions described (1 ml absorbent per 1 IU or PK). However, in order to prepare large quantities of enzyme, a number of dye-affinity absorbents were tried in our laboratory, and it was discovered that using Red A (Amicon) works well under optimized conditions. For exemplary purposes only, the detailed procedures for using Red A column are discussed below.

Purification of Pyruvate Kinase from Human Whole Blood:

Human whole blood required to isolate the enzyme was obtained from the Medical College of Virginia's Blood bank. All purification steps were carried out at 4° C. ADP, PEP, NADH, LDH, and all buffer salts were obtained from Sigma Chemicals, Inc. All buffers contain 10% (V/V) glycerol, 2 mM β mercaptoethanol (β-ME), 10 mM EDTA, 10 mM 4-aminocaproic acid (ACA), and 1 mM phenylmethanesulfonylfluoride (PMSF). The following three buffers were used during the isolation and purification of the enzymes from whole blood.

Buffers:
A: 10 mM TRIS, 80 mM ME, pH 7.5
B: 10 mM TRIS, 800 mM KCl, 1 mM ME, 0.5 mM $MgSO_4$, pH 7.5
C: 20 mM TRIS, 800 mM KCl, 1 mM ME, 1 mM EDTA, 1 mM FDP, pH 7.5

The four units of human whole blood obtained from the Blood Bank were mixed with 2 vol. gelatin solution (10 mg/ml heparin) and 1 vol. 145 mM NaCl, centrifuged at 4000 g for 15 min., and the residual buffy coat was eliminated. The washed red cells were mixed with 2 vol. $H_2O$ containing 2 mM ME, 10 mM EDTA, 10 mM ACA, 2 mM PMSF and 10% cold toluene, homogenized for 1 min with a blender homogenizer, and centrifuged for 30 min at 10,000 g. The upper layer (fat containing) was discarded and the hemolysate was decanted into a beaker. Under gentle agitation, solid $(NH_4)_2SO_4$ (23 g/100 ml) was slowly added into the hemolysate, and the mixture was incubated at 4° C. for 2 hrs. The precipitate was collected by centrifugation at 10,000 g for 30 min. The pellets were collected and dissolved by adding 11 g/100 ml $(NH_4)_2SO_4$ adjusted to pH 8.0 with solid TRIS, centrifuged, and the supernatant was then collected while discarding the residual pellets. To this supernatant was then added solid $(NH_4)_2SO_4$ to get 22 g/100 ml final concentration. The pH was adjusted to 6.6 with 10% acetic acid and the solution was centrifuged at 10,000 g for 30 min to collect the precipitate. The precipitate was washed one more time with 21 g/100 ml $(NH_4)_2SO_4$, pH 6.6, and centrifuged to collect the pellets. The pellets were then dissolved in buffer A, centrifuged at 26,000 g for 30 min to collect the clear supernatant. The total protein and PK concentrations were measured at an optical density of 280 nm and 340 nm, respectively.

The crude isolated PK (100 ml of 3 mg/ml sample containing about 1 mg PK) was then loaded onto a Amicon Red A column (5×35 cm) equilibrated with Buffer A. The column was washed with 500 ml Buffer A, then with Buffer B until absorbency at 280 nm disappeared with no detectable PK activity in the flow through. The enzyme was eluted with 1.5 L Buffer C with a flow rate of 2–5 ml/min, by collecting into all 10 ml fractions. The PK activity of each fraction was then measured and all active fractions were pooled together. The pooled fractions were concentrated into a final vol. of 15–25 ml with an Amicon ultrafiltration concentrator. All concentrated enzyme fractions were then transferred into a dialysis membrane bag and dialyzed against 3×300 ml Buffer A. The PK can also be precipitated by dialyzing against 50 mM TRIS, pH 7.5 containing 35 g/100 ml $(NH_4)_2SO_4$. Pellets should be stored under −70° C. The overall yield of the enzyme isolation and purification using this process is 0.5–1.0 mg.

The purity of the preparation was assessed by SDS-PAGE. A typical result of the preparation shows three major bands around 62, 58 and 54 kD. The result is largely consistent with the reported values. The three bands are estimated to be larger than 90% of the total proteins.

EXAMPLE 2

Measurement of PK Activity

Figure 1:
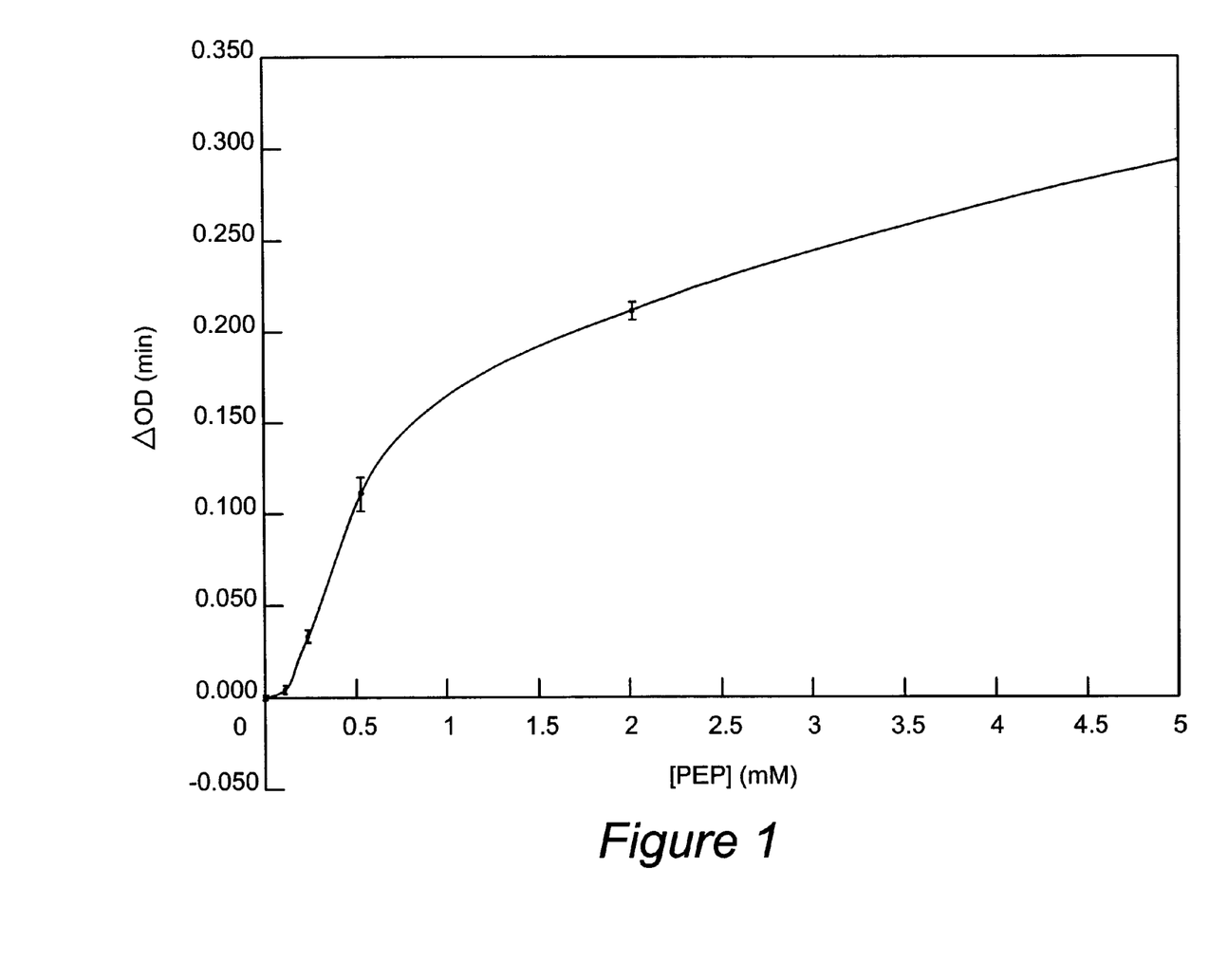
FIG. 1 is a saturation plot as discussed in Example 2 where optical density is measured against various concentrations of PEP. It can be seen that the saturation point is reached when the change in optical density/min is approximately 0.3. In all experiments with the allosteric compounds identified herein, the saturation point was reached prior to addition of the allosteric compound.

PK activity was measured using the assay conditions that are recommended by the International Committee for Standardization in Hematology (ICSH). FIG. 1 shows the saturation curve of PK with respect to PEP. The positive cooperativity of substrate binding is clearly seen from the upward curvature in the Lineweaver plot. The experimental data were fit to the Hill equation. The derived parameters were $K_{0.5S}$=2.37 mM and Hill coefficient ($n_H$) of 1.41.

Figure 2:
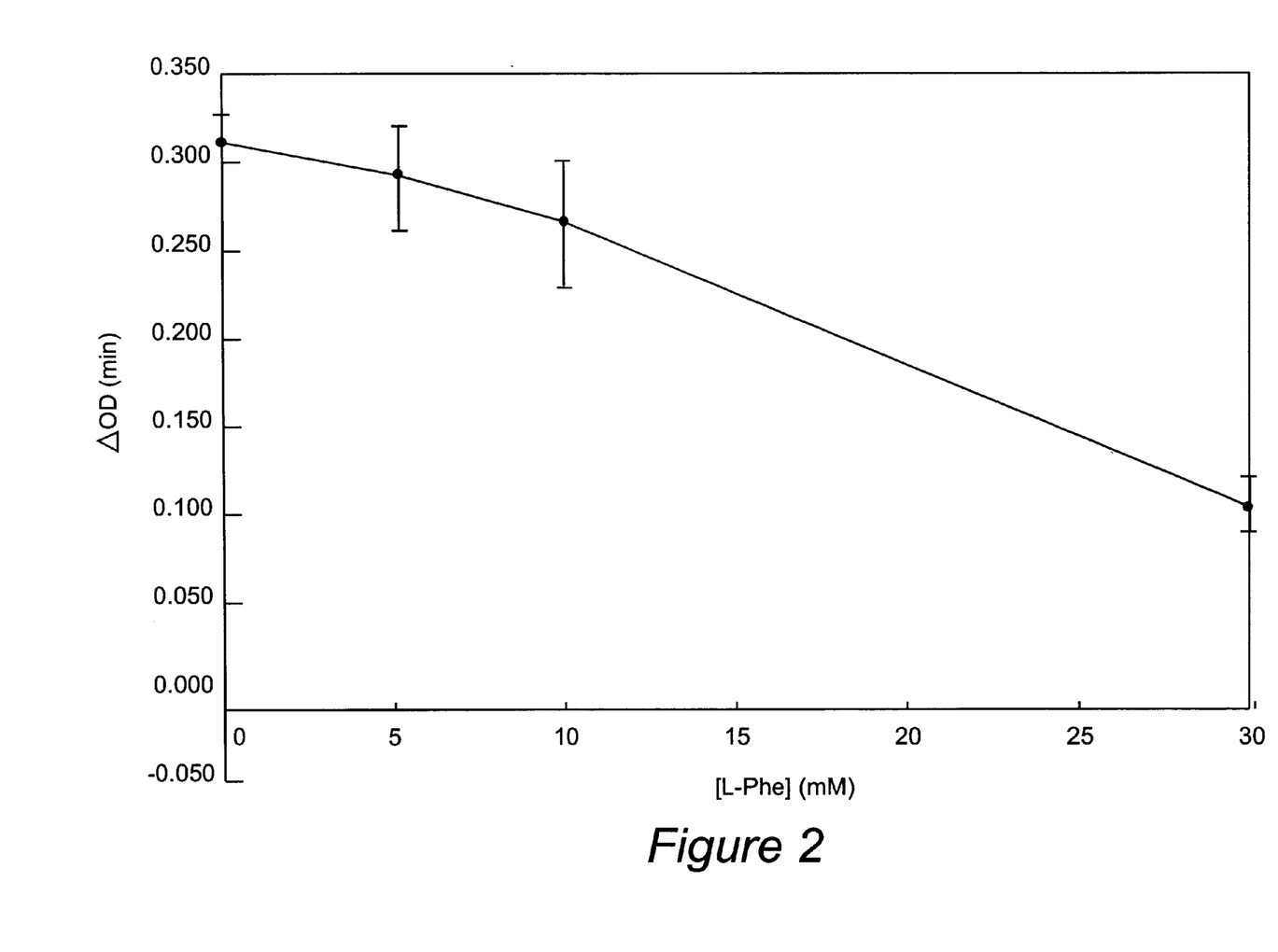
FIG. 2 is a plot of varying concentrations of phenylalanine versus optical density measurements. As discussed in Example 2, phenylalanine is an inhibitor of PK. The decline in optical density shown in FIG. 2 shows that increasing concentrations of phenylalanine result in increasing inhibition of the PK enzyme.

Phenlyalanine has long been known as an allosteric inhibitor of PK. FIG. 2 shows the PK activity measured in the presence of four different concentrations of phenlyalanine. It can be seen from FIG. 2 that an increase in the concentration of phenylalanine results in a decreased affinity and a more pronounced sigmoidity of the substrate binding. When phenylalanine increases from 0 to 30 mM, the $K_{0.5S}$ increases by 2.5 folds and $n_H$ increases by 1.4 folds, respectively. To avoid fluctuations in measurement of PK parameters, all experiments reported herein and assays were performed using the same batch of preparation and under identical conditions.

Measurement of PK Activity of Human Erythrocyte Pyruvate Kinase (R-PK):

PK activity is measured by coupling it with lactate dehydrogenase, which transforms pyruvate into lactate and oxidizes NADH into NAD. A reduction of oxidation of NADH is followed at 340 nm using the 96 well plate in a Spectramax spectrophotometer (Molecular Devices, Ca.).

The assay buffer (100 mM Tris pH 7.5) was prepared by dissolving TRIS 100 mM, KCl 100 mM, EDTA 0.5 mM, and 10 MM $MgCl_2$ in deionized water. The pH of the solution was adjusted to 7.5 by adding a small amount of TRIS. The stock solution of NADH (20 mM), ADP 100 mM (neutralized), LDH 500 IU/ml and PEP 100 mM were prepared in the assay buffer. The following quantities of reagents were added to make 1 ml of assay solution.

| Final Concentration | | |
|---|---|---|
| Assay Buffer | 910 µl | |
| NADH | 10 µl | 0.2 mM |
| ADP | 15 µl | 1.5 mM |
| LDH | 2 µl | 1 IU |
| PK | 10 µl | |

The contents were mixed and incubated for five minutes at 37° C. Then, 50 µl of PEP was added and the absorbance changes were followed at 340 nm. The initial reaction velocity in AU/min was then calculated.

The incubation of human erythrocyte PK with various allosteric modulators in the assay buffer (pH 7.5) or in DMSO solution at different concentrations and at 37° C. resulted in a concentration dependent inhibition or activation of the enzyme. The phenylalanine was used as a standard reference for the inhibition activity assay, and results are presented in FIG. 2 and Table 1. The control samples in each experiment were incubated under the same conditions as without any compound. In all cases, the experiments were begun after saturation with PEP. The percent inhibition of PK activity was calculated by subtracting the activity of the control sample from the activity in the presence of compound. The activity data for various compounds are presented in Table 1 where Table 1 shows compounds, which demonstrate allosteric inhibition of PK.

EXAMPLE 3

TB 32—

Figure 3A:
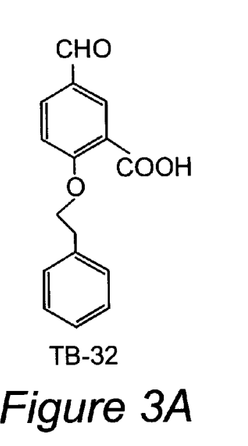

2-phenylethyloxy-5-formylbenzoic acid, identified as TB 32, is shown in FIG. 3a. The synthesis of this compound is described in detail in U.S. Pat. No. 5,599,974, which is herein incorporated by reference. Methyl-2-hydroxy-5-acetalbenzoate (1.0 g, 4.46 mmol), 2-phenylethylbromide (0.98 g, 5.27 mmol) and powdered potassium carbonate (2.0 g, 14.5 mmol) in dry acetone were heated to reflux for twelve hours. The reaction mixture was filtered while hot and the solvent was removed under vacuum. The crude product was flash chromatographed using hexane-ethyl acetate mixtures and the desired intermediate, methyl-2-phenylethyloxy-5-acetalbenzoate in 10% potassium hydroxide (20 ml) was heated to reflux for 1 hr. The reaction mixture was filtered, cooled and acidified with concentrated hydrochloric acid. The precipitate was filtered, washed thoroughly with water (40 ml), re-dissolved in hot aqueous solution of sodium bicarbonate and extracted with diethyl ether (2×20 ml). The aqueous layer was acidified, the product filtered, washed with small amounts of diethyl ether, and air dried. Yield 80%; mp 112–114° C.; $^1$H NMR (DMSO-$d_6$) δ 13.05 (s, 1H, $CO_2H$), 9.92 (s, 1H, CHO), 8.19 (d, 1H, ArH), 8.01 (dd, 1H, ArH), 7.2–7.45 (m, 6H, ArH), 4.35 (t, 2H, $CH_2$) 3.05 (t, 2H, $CH_2$); Anal. Calcd. for ($C_{16}H_{12}O_4 \cdot 0.25H_2O$) C 69.94, H 5.32, found C 70.29, H 5.28.

TB 88—

Figure 3B:
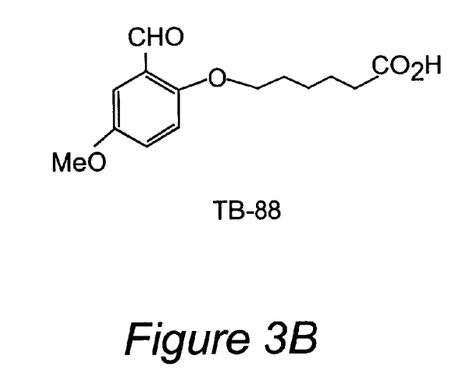

6-(2-formyl-4-methoxyphenoxy)hexanoic acid, identified as TB 88, is shown in FIG. 3b. 2-hydroxy-5-methoxybenzaldehyde (1.52 g, 10 mmol), methyl 6-bromohexanoate (2.08 g, 10 mmol), and anhydrous potassium carbonate (2.0 g, 14.5 mmol) were stirred in anhydrous DMF (50 mL) at 60° C. for 24 hours. The reaction mixture was filtered and the filtrate diluted with 50 mL ethyl acetate, washed twice with 200 mL water, dried over anhydrous $Na_2SO_4$ and evaporated to dryness under reduced pressure. The intermediate solid ester (2.80 g, 10 mmol) was hydrolyzed by stirring it in the presence of 10% potassium hydroxide (2/1: water/ethanol) at room temperature for 2 hours (i.e., stage 2A). The ethanol was removed under reduced pressure and the basic aqueous phase extracted with ethyl acetate. The desired aldehyde acid was precipitated from the alkaline solution by acidification and the precipitate filtered, washed with copious amounts of water and oven dried at 70° C. 2.61 g (98% yield; m.p. 104–106° C.) of 6-(2-formyl-4-methoxyphenoxy)hexanoic acid product, designated as compound TB88, was obtained with the structure of the product confirmed by NMR and IR spectroscopy and elemental analysis.

Compound TB 154 was prepared from the corresponding starting material, hydroxy-substituted benzladehyde and methyl bromohexanoate, by following the procedure described herein for TB88.

TB 154—

Figure 3C:
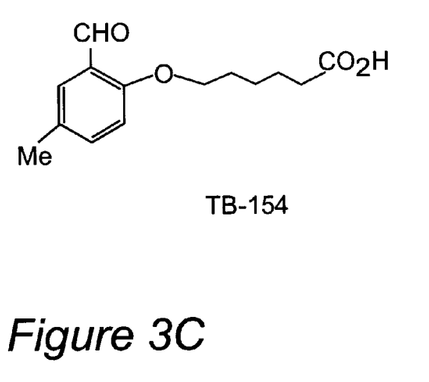
Figure 3D:
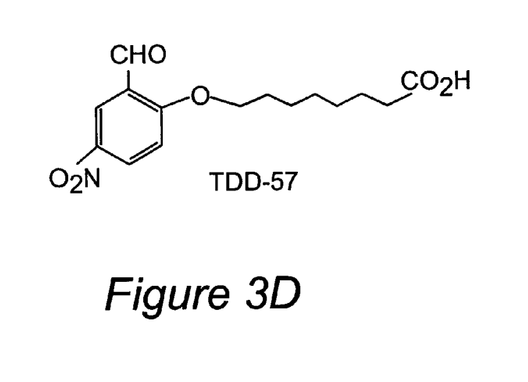

6-(2-formyl-4-methylphenoxy)hexanoic acid, identified as TB154 and shown in FIG. 3c was synthesized using 2-hydrocy-5-methylbenzaldehyde (1.36 g, 10 mmol) and methyl 6-bromohexanoate (2.08 g, 10 mmol) as starting materials with a yield of 2.33 g (93%). The compound melted at 97–99° C. and its structure was confirmed by NMR. Anal. Calcd for $C_{14}H_{18}O_4$: C, 67.17, H, 7.26. Found C, 67.27; H, 7.24.

TDD 57—

6-(2-formyl-4-nitrophenoxy)octanoic Acid, identified as TDD-57 was prepared as follows: 2-Hydroxy-5-nitrobenzaldehyde (1.67 g, 10 mmol), methyl 8-bromooctanate (2.64 g. 12 mmol), and anhydrous potassium carbonate in anhydrous acetonitrile (40 mL) were stirred at 70° C. under nitrogen overnight. The cooled reaction mixture was diluted with ethyl acetate (60 mL) and washed with water (2×30 mL), brine (30 mL), dried ($MgSO_4$) and evaporated to dryness under reduced pressure. To the intermediate ester (1.4 g, 4.3 mmol) in ethanol (30 mL) was added 10% sodium hydroxide (10 mL) and stirred at room temperature for 4 hr. The ethanol was removed under reduced pressure, the aqueous phase diluted with water (50 µL) and extracted with ethyl acetate (2×40 mL). The aqueous phase was acidified with dilute hydrochloric acid, the product extracted with ethyl acetate (3×40 mL), the organic phase washed with brine (30 mL), dried ($MgSO_4$) and evaporated to dryness under reduced pressure to give 1.2 g (90%) of the titled compound. Melting point 102–103° C. The structure of the product was confirmed by NMR. Anal. Calcd. for $C_{15}H_{19}NO_6$: C, 58.25; H, 6.19; N, 4.53; Found: C, 58.04; H, 6.33; N, 4.38.

CA-GSK-2

Figure 3E:
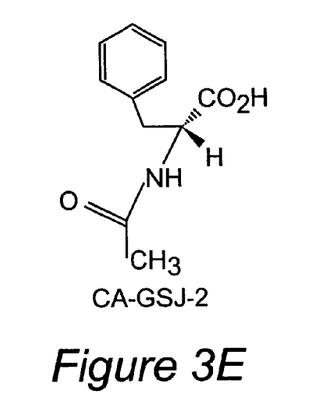
Figure 3F:
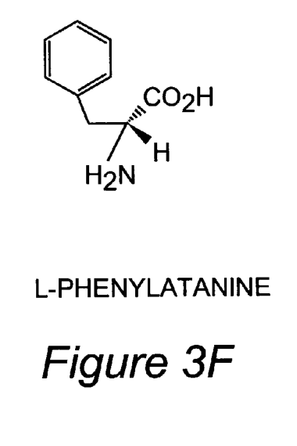
Figure 4A:
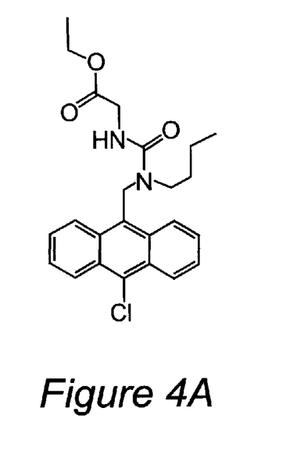
FIG. 4 shows chemical structures of 12 more allosteric inhibitors of PK activity.
Figure 4B:
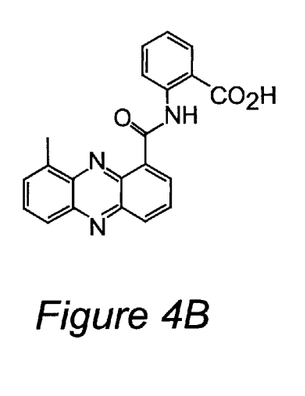
Figure 4C:
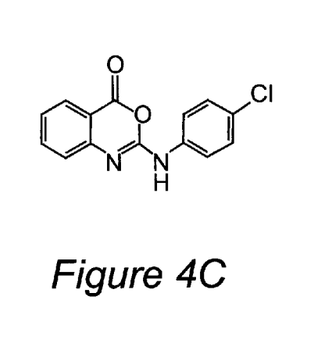
Figure 4D:
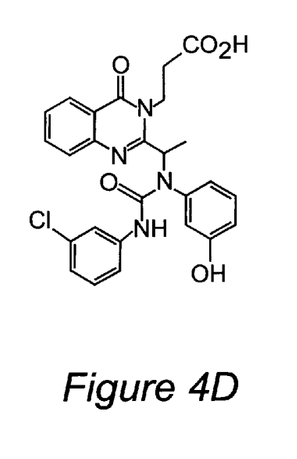
Figure 4E:
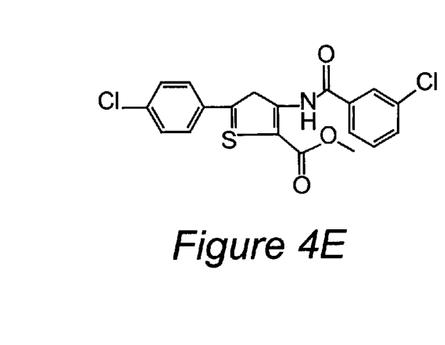
Figure 4F:
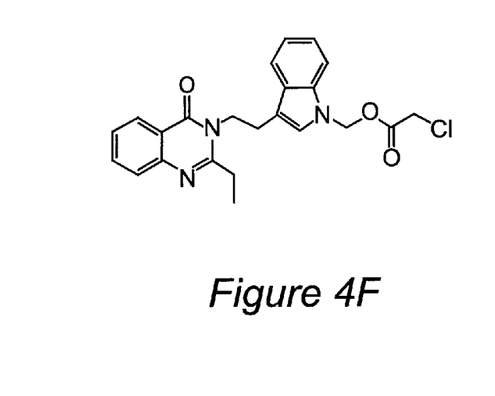
Figure 4G:
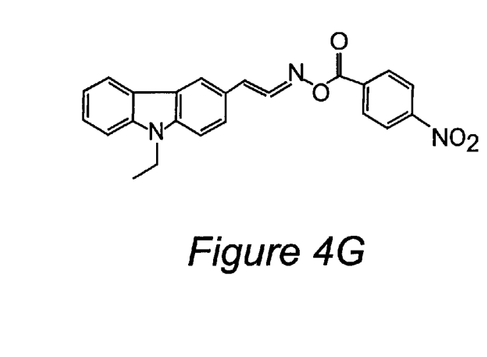
Figure 4H:
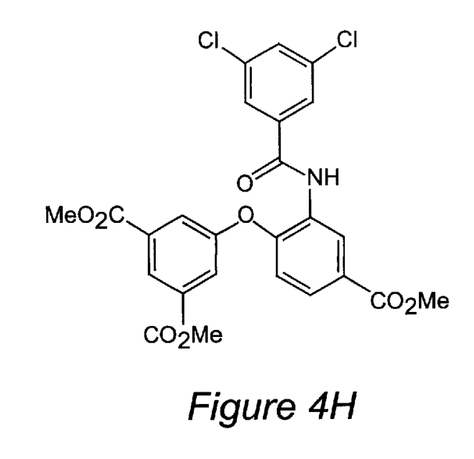
Figure 4I:
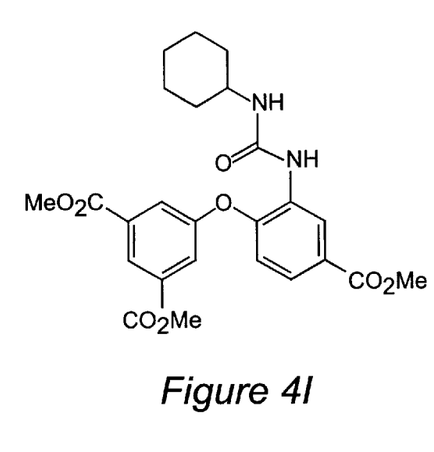
Figure 4J:
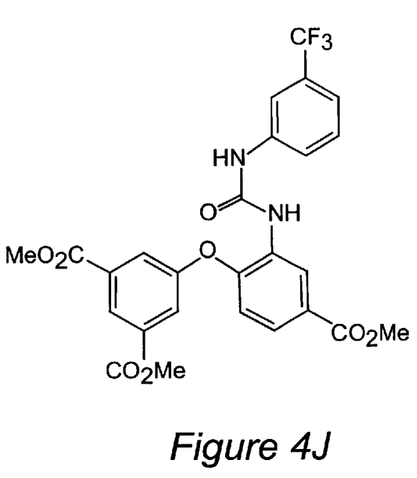
Figure 4K:
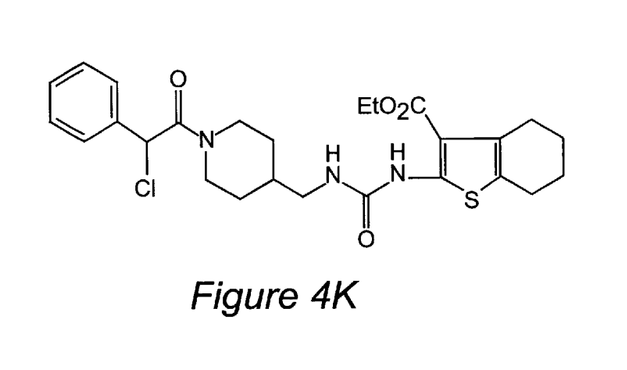
Figure 4L:
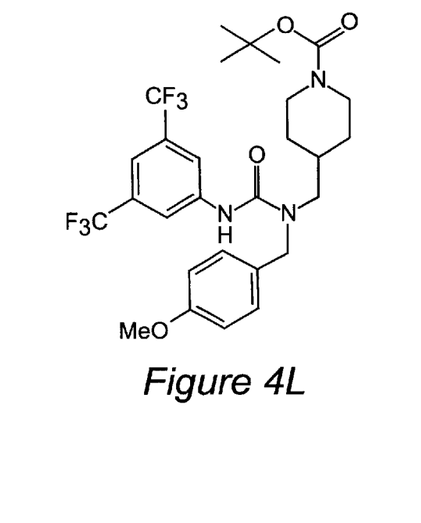

CA-GSJ-2, shown in FIG. 3e was purchased from the Aldrich Chemical Company and is commercially available.

EXAMPLE 4

The compounds shown in FIG. 4 are commercially available and were purchased from a combinatorial database of Comgenex, Inc., as follows:

compound 4(1)([3-Butyl-3-(10-chloro-anthracen-9-ylmethyl)-ureido]-acetic acid ethyl ester)

compound 4(2)(2-[(9-Methyl-phenazine-1-carbonyl)-amino]-benzoic acid)

compound 4(3)(2-(4-Chloro-phenylamino)-benzo[d][1,3]oxazin-4-one)

compound 4(4)(3-(2-{1-(3-Chlorophenyl)-1(3-hydroxyphenyl)-ureido]-ethyl}-4-oxo-4H-quinazolin-3-yl)-propionic acid)

compound 4(5)(2-(9-Ethyl-9H-carbazol-3-ylvinylideneamino)-1-(4-nitrobenzoate)

compound 4(6)(Chloroacetic acid 3-[2-(2-ethyl-4-oxo-4H-quinazolin-3-yl)ethyl]-indol-lylmethylester)

compound 4(7)(3-Benzylamino-5-(4-chlorophenyl)-4H-1$\lambda^4$-thiophene-2-carboxylic acid methyl ester)

compound 4(8)(5-[2-(3,5-Dichlorobenzoylamino)-4-methoxycarbonyl -phenoxy]-isophtahlic acid dimethyl ester)

compound 4(9)(5-[2-(3-Cyclohexyl-ureido)-4-methoxycarbonyl -phenoxy]-isophtahlic acid dimethyl ester)

compound 4(10)(5-{4-Methoxycarbonyl-2-[3-(3-trifluoromethyl-phenylureido]-phenoxy}-isophtahlic acid dimethyl ester)

compound 4(11)(4-[3,5-Bistrifluoromethylphenyl)-1-(4-methoxybenzl) -ureidomethyl]-piperidine-1-carboxylic acid ter-butyl ester)

compound 4(12)(2-{3-[1-(2-Chloro-2-phenylacetyl)-piperidn-4-ylmethylureido}-4,5,6,7-tetrahydrobenzo[b]thiophene-3-carboxylic acid ethyl ester)

Compounds 4(1) through 4(12) thus obtained were tested. R-PK inhibition results for compounds 4(1) through 4(12), expressed as percentage of initial PK activity, are shown in FIG. 5.

Figure 5:
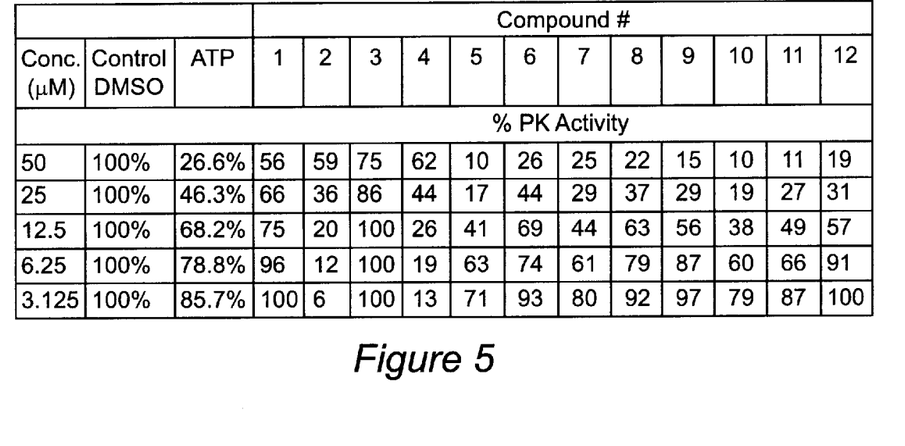
FIG. 5 is a table of dose-response for R-PK of compounds shown in FIGS. 4(a)–(l).

The percent activity values presented in FIG. 5 represent an average of six independent experiments. All examined compounds were prepared as stock solutions in DMSO. Consequently, DMSO alone was assayed to ensure that it does not, by itself, change the enzyme's activity. As observed in FIG. 5, the examined compounds possessed a wide range of R-PK inhibitory activity (from 58% inhibition to 98% inhibition) at micro molar concentration. Interestingly, many of these molecules displayed stronger R-PK inhibition, at much lower concentrations, than previously reported L-alanine and L-phenylalanine. Another encouraging finding was that these compounds exhibited sigmoidal R-PK inhibition plots, indicating that their mode of action was indeed allosteric.

These results will allow for the initiation of structure-activity studies in the laboratory.

Figure 6:
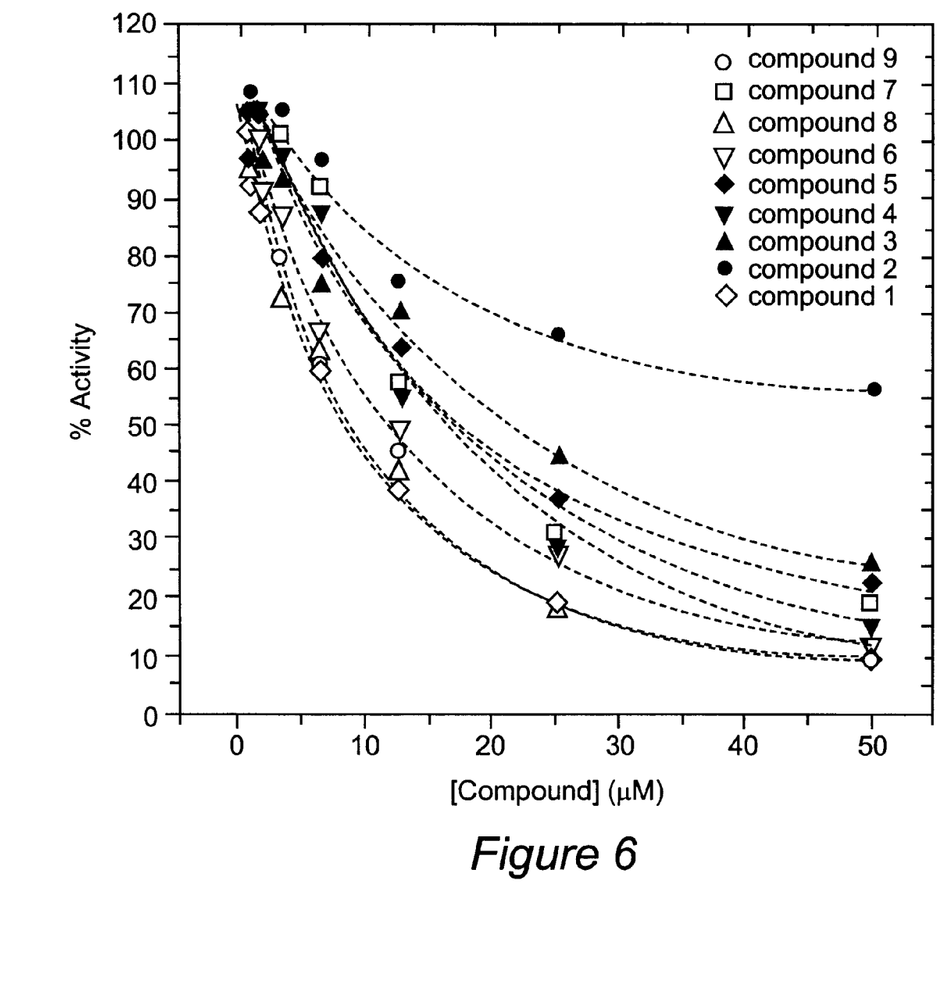
FIG. 6 is a plot for Dose-Response of Selected Compounds and for each of nine compounds, shows concentration versus % activity.

$IC_{50}$'s for these compounds are presented in Table 2. As observed in FIG. 6, the present inventors have identified compounds that inhibit R-PK in a dose dependent manner at uM concentrations.

TABLE 2

$IC_{50}$ Concentrations for Selected Compounds

| Compound | $IC_{50}$ (uM) |
|---|---|
| (1) | >50 |
| (2) | 8.9 |
| (3) | 20.9 |
| (4) | 16.1 |
| (5) | 17.4 |
| (6) | 12.1 |
| (7) | 16.9 |
| (8) | 9.0 |
| (9) | 9.4 |

Thus, above nine R-PK inhibitors exhibited a dose dependent response to R-PK.

As a control for FIG. 5, the assay was performed with DMSO, but no compound.

In FIG. 5, the column shown for "ATP" reports inhibition by ATP, which was also measured to validate the assay reliability.

Otherwise, the dose-response for R-PK in FIG. 5 in this Example 5 was performed as described in the above Examples.

In view of the data in FIG. 5, compounds 4(1)–(12) are suitable for allosterically modifying pyruvate kinase in a patient, by providing a patient in need thereof with a sufficient quantity of such compound, or its salt or other derivative.

Derivatives of compounds 4(1)–(12) can be made which will also exhibit the same or enhanced allosteric effects on PK. These derivatives might advantageously be formed at the carboxylic acid moiety (by replacement of the hydrogen), but may also be configured at the aldehyde or be ionic in nature. These derivatives can include the substitution of salt or metal cations for hydrogen groups, such as sodium, potassium, lithium, ammonium, and alkali and alkaline metals (Mn and Mg, etc), or the formation of ester or ether derivatives at the hydrogen groups such as $C_1$–$_{12}$ alkyl groups, or involve similar substitutions.

The current active molecules can be modified via substitution with alkyl, alkoxy, halo and suitably substituted aromatic moieties to enhance their R-PK inhibition potency.

For administering to a patient, the compound, or its salt, or a derivative of the compound, may be formulated into usual pharmaceutical dosage forms. An important aspect of R-PK inhibition involves identifying compounds that will effectively inhibit this enzyme to increase red cell 2,3 DPG levels at least 2 to 3 fold. Based on R-PK allosteric inhibition produced by the compounds in Table 2, it appears that it will be feasible to significantly inhibit R-PK activity, which should result in significant increases in 2,3-DPG concentrations in erythrocytes.

Hereditary deficiencies in PK cause hemolytic anemia. In these individuals, 2,3 DPG levels are increased 2–3 fold, estimated as a shift of to 15 mm Hg right shift in the oxygen-binding curve. This is a very significant increase in oxygen level to hypoxic tissues in the range of that observed clinically for the compound RSR-13. Although the window for altering 2,3-DPG levels without incurring adverse side effects appears small (2–3 fold), it is easy to titrate, as we have seen with clinical RSR-13 studies where dosage is easily followed by the subsequent shift in the oxygen-binding curve.

Since we are targeting an erythrocyte enzyme PK, which is present in much lower concentration as compared to the hemoglobin concentration in red blood cells, the doses required to modulate the activity of PK would also be smaller. As a result, it is possible to formulate these compounds as an oral therapeutic agent.

While the invention has been described in terms of its preferred embodiments, those skilled in the art will recognize that the invention can be practiced with modification within the spirit and scope of the appended claims.

We claim:

1. A method for allosterically modifying pyruvate kinase in a patient, comprising the step of providing a patient in need thereof with a sufficient quantity of a compound which inhibits pyruvate kinase activity, wherein said compound is selected from the group consisting of

[3-Butyl-3-(10-chloro-anthracen-9-ylmethyl)-ureido]-acetic acid ethyl ester;

2-[(9-Methyl-phenazine-1-carbonyl)-amino]-benzoic acid;

2-(4-Chloro-phenylamino)-benzo[d][1,3]oxazin-4-one;

3-(2-{1-(3-Chlorophenyl)-1(3-hydroxyphenyl)-ureido]-ethyl}-4-oxo-4H-quinazolin-3-yl)-propionic acid;

2-(9-Ethyl-9H-carbazol-3-ylvinylideneamino)-1-(4-nitrobenzoate);

Chloroacetic acid 3-[2-(2-ethyl-4-oxo-4H-quinazolin-3-yl)ethyl]-indol-lylmethylester;

3-Benzylamino-5-(4-chlorophenyl)-4H-1$\lambda^4$-thiophene-2-carboxylic acid methyl ester;

5-[2-(3,5-Dichlorobenzoylamino)-4-methoxycarbonyl-phenoxy]-isophtahlic acid dimethyl ester;

5-[2-(3-Cyclohexyl-ureido)-4-methoxycarbonyl-phenoxy]-isophtahlic acid dimethyl ester;

5-{4-Methoxycarbonyl-2-[3-(3-trifluoromethylphenylureido]-phenoxy}-isophthalic acid dimethyl ester;

4-[3,5-Bistrifluoromethylphenyl)-1-(4-methoxybenzyl)-ureidomethyl]-piperidine-1-carboxylic acid ter-butyl ester;

2-{3-[1-(2-Chloro-2-phenylacetyl)-piperidn-4-ylmethylureido}-4,5,6,7-tetrahydrobenzo[b]thiophene-3-carboxylic acid ethyl ester;

and pharmaceutically acceptable salts thereof.

2. A method according to claim 1, wherein the compound is [3-Butyl-3-(10-chloro-anthracen-9-ylmethyl)-ureido]-acetic acid ethyl ester or 2-[(9-Methyl-phenazine-1-carbonyl)-amino]-benzoic acid.

3. A method according to claim 1, wherein the compound is 2-(4-Chloro-phenylamino)-benzo[d][1,3]oxazin-4-one.

4. A method according to claim 1, wherein the compound is 3-(2-{1-(3-Chlorophenyl)-1(3-hydroxyphenyl)-ureido]-ethyl}-4-oxo-4H-quinazolin-3-yl)-propionic acid.

5. A method according to claim 1, wherein the compound is 2-(9-Ethyl-9H-carbazol-3-ylvinylideneamino)-1-(4-nitrobenzoate.

6. A method according to claim 1, wherein the compound is Chloroacetic acid 3-[2-(2-ethyl-4-oxo-4H-quinazolin-3-yl)ethyl]-indol-1ylmethylester.

7. A method according to claim 1, wherein the compound is 3-Benzylamino-5-(4-chlorophenyl)-4H-1$\lambda^4$-thiophene-2-carboxylic acid methyl ester.

8. A method according to claim 1, wherein the compound is 5-[2-(3,5-Dichlorobenzoylamino)-4-methoxycarbonyl-phenoxy]-isophthalic acid dimethyl ester.

9. A method according to claim 1, wherein the compound is 5-[2-(3-Cyclohexyl-ureido)-4-methoxycarbonyl-phenoxy]-isophtahlic acid dimethyl ester.

10. A method according to claim 1, wherein the compound is 5-{4-Methoxycarbonyl-2-[3-(3-trifluoromethylphenylureido]-phenoxy}-isophtahlic acid dimethyl ester.

11. A method according to claim 1, wherein the compound is 4-[3,5-Bistrifluoromethylphenyl)-1-(4-methoxybenzyl)-ureidomethyl]-piperidine -1-carboxylic acid ter-butyl ester.

12. A method according to claim 1, wherein the compound is 2-{3-[1-(2-Chloro-2-phenylacetyl)-piperidn-4-ylmethylureido}-4,5,6,7-tetrahydrobenzo[b]thiophene-3-carboxylic acid ethyl ester.

* * * * *